(12) United States Patent
Mestais et al.

(10) Patent No.: US 6,365,900 B1
(45) Date of Patent: Apr. 2, 2002

(54) SENSING HEAD AND COLLIMATOR FOR GAMMA-CAMERA

(75) Inventors: Corinne Mestais, La Terrasse; Raymond Campagnolo, Grenoble; Robert Allemand, Saint Ismier, all of (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/331,582

(22) PCT Filed: Dec. 29, 1997

(86) PCT No.: PCT/FR97/02438
§ 371 Date: Jun. 30, 1999
§ 102(e) Date: Jun. 30, 1999

(87) PCT Pub. No.: WO98/29764
PCT Pub. Date: Jul. 9, 1998

(30) Foreign Application Priority Data

Dec. 30, 1996 (FR) ................................. 96/16199

(51) Int. Cl.$^7$ ................................................. G21K 1/02
(52) U.S. Cl. ..................... 250/363.1; 378/147; 378/154
(58) Field of Search ................................. 378/147, 363.1, 378/363.02; 250/363.1, 363.02

(56) References Cited

U.S. PATENT DOCUMENTS

| | | | |
|---|---|---|---|
| 3,011,057 A | | 11/1961 | Anger |
| 4,047,037 A | * | 9/1977 | Schlosser et al. |
| 5,276,615 A | | 1/1994 | Edmond et al. |
| 5,371,362 A | | 12/1994 | Mestais et al. |
| 5,591,564 A | * | 1/1997 | Rostoker et al. ............ 430/311 |
| 5,786,597 A | * | 7/1998 | Lingren et al. |
| 6,194,726 B1 | * | 2/2001 | Pi et al. .................... 250/363.1 |

* cited by examiner

Primary Examiner—David P. Porta
Assistant Examiner—Pamela R. Hobden
(74) Attorney, Agent, or Firm—Oblon, Spivak, McClelland, Maier & Neustadt, P.C.

(57) ABSTRACT

A detection head and collimator for a gamma camera. The detection head includes several elementary detectors with semiconductors adjacent to each other to form a detection plane. The collimator is placed in front of the detection plane and includes a number of ducts laid out in a repetition pattern. The shape of the elementary detectors and the repetition pattern are rectangular in the detection plane.

7 Claims, 6 Drawing Sheets

SENSING HEAD AND COLLIMATOR FOR GAMMA-CAMERA

BACKGROUND OF THE INVENTION

This invention relates to a detection head and a collimator for a gamma camera and more particularly for a "pixels" gamma camera.

A pixels gamma camera means a camera sensitive to gamma radiation, in which the detection head comprises a number of adjacent individual elementary detectors.

The invention has applications in medical imagery, as for example such as scintigraphy and Single Photo-Emission Computed Tomography (SPECT).

DISCUSSION OF THE BACKGROUND

Gamma cameras conventionally used in medical imagery are of the Anger type. Document (1), listed in the references at the end of this description, contains further information about this subject.

Gamma cameras are used particularly to display the distribution of molecules marked by a radioactive isotope previously injected into the patient, throughout the body or in an organ.

FIG. 1 more precisely shows a detection head 10 of an Anger type gamma camera placed facing an organ 12.

The detection head 10 comprises a collimator 20, a scintillator crystal 24, a light guide 22 and several photo-multiplier tubes 26 placed adjacent to each other in order to cover one surface of the light guide 22 opposite the scintillator crystal 24. For example, the scintillator may be an NaI(Tl) crystal.

The collimator is in the form of a lead disk through which a number of ducts 21 carrying gamma radiation can pass, approximately identical and parallel to each other. The disk is placed in contact with the scintillator 24 such that the ducts 21 are perpendicular to the surface of this crystal. A divergent or convergent collimator may be used for some applications in which the object size has to be magnified or reduced to produce the image size.

The function of the collimator 20 is to select the part of the gamma radiation 30 emitted by organ 12 that reaches the detection head at approximately normal incidence.

The selective nature of the collimator is such that the resolution and sharpness of the image produced can be increased. However, the resolution is increased at the detriment of sensitivity.

The opening and the length of the ducts 21 are determined as a function of the inspection energy and the compromise between the spatial resolution and the derived sensitivity. As the ducts become longer and narrower, the spatial resolution of the detection head improves but its sensitivity reduces. Furthermore, the spacing between ducts is chosen to be higher when the energy of the received radiation is greater.

Known collimator ducts have a hexagonal cross-section (or round for high energies).

This form is dictated partly by detection uniformity requirements, but also by collimator manufacturing constraints.

It is considered that the circular shape for the collimator duct cross-section gives the most uniform and homogeneous detection possible.

However, when ducts with a circular cross-section are placed adjacent to each other, it is observed that the thicknesses of the material walls separating the ducts are not uniform. The non-uniform nature of the wall thicknesses and especially the existence of intermediate regions between the ducts in which the thickness of the absorbing material (lead) varies, is a major disadvantage.

Doses of radioactive product injected into the patient necessarily have to be limited. Thus, the intensity of the emitted radiation is relatively low. Under these conditions, the extent and thickness of intermediate walls separating the collimator ducts must be reduced in order to limit excessive losses of the "useful" radiation.

In order to limit the thickness of the walls between ducts and differences in this thickness, collimators are made with ducts with a hexagonal cross-section. This shape also has the advantage that it facilitates manufacturing of the collimators.

Finally, it can be noted that the hexagonal shape is used to the extent that it is relatively close to the circular shape, and enables approximately uniform detection.

In the case of ducts with a hexagonal cross-section, the thickness of the walls that delimit the ducts is usually chosen within a range from 0.2 to 2 mm. The characteristic size of the duct opening, in other words the distance between flats in the hexagonal cross-section, is of the order of 1.5 to 4.5 mm. Finally, the depth of the ducts is usually chosen between 30 and 50 mm.

Known collimators are usually made using a technique for the assembly of lead sheets shaped to make the ducts. According to another known technique, the collimators may also be obtained by casting in a pin mold.

With reference to FIG. 1, it can be seen that gamma photons that have passed through the collimator reach the scintillator crystal 24 in which practically every gamma photon is converted into several light photons 31. Throughout the rest of this text, each detected interaction between a gamma photon and the detector material, for example with the scintillator crystal, will be denoted as an "event".

Photo-multipliers 26 are designed to emit an electric pulse proportional to the number of light photons received on scintillator 24, at each event.

In order to be able to locate the scintillation event more precisely, the photo-multipliers 26 are not placed immediately adjacent to scintillator crystal 24, but are separated from it by the light guide 22.

The photo-multipliers emit a signal, the amplitude of which is proportional to the total quantity of light produced in the scintillator by gamma radiation, in other words proportional to its energy. However, the individual signal from each photo-multiplier also depends on the distance that separates it from the interaction point 30 of the gamma radiation with the scintillator material. Each photo-multiplier outputs a current pulse proportional to the light flux that it received. In the example shown in FIG. 1, small graphs A, B, C show that: the photo-multipliers 26a, 26b and 26c located at different distances from an interaction point 30 output signals with different amplitudes.

The position of the interaction point 30 and the energy of a gamma photon is calculated in the gamma camera starting from signals originating from all photo-multipliers by making a center of gravity weighting of the contributions of each photo-multiplier.

However, Anger type gamma cameras have a disadvantage due to the fact that the number of light photons created during each event in the scintillator crystal satisfies Poisson statistics. The number of photo-electrons torn from the photo-cathode of the photo-multipliers also satisfies Poisson statistics. Thus, the position and energy calculations are affected by an inaccuracy related to Poisson fluctuations in the number of light photons and the number of photoelectrons produced for each event.

The standard deviations of the fluctuations is lower when the number of photons or photoelectrons is high. The inherent spatial resolution of the gamma camera is characterized by the width at mid-height of the distribution of the calculated positions, for a single isolated collimated point source placed on the crystal. The resolution is of the order of 3 to 4 mm at 140 keV. Furthermore, the energy of the gamma photon is calculated by taking the sum of the contributions of all photo-multipliers that received light. This is also affected by a statistical fluctuation. The energy resolution is characterized by the ratio of the mid-height width of the distribution of calculated energies, to the average value of the distribution, for the same source. It is of the order of 9 to 11% at 140 keV.

Detection heads for gamma cameras are also known in which the scintillator crystal and photo-multipliers are replaced by solid detectors arranged in the form of a matrix of individual detectors. In this case, the spatial resolution of the gamma camera depends on the size of the individual detectors.

The attached FIG. 2 very diagrammatically shows a detection head with solid detectors, for information. The detection head 40 comprises several individual elementary detectors 42 with semi-conductors. For example, they may be CdTe or CdZnTe type detectors. Individual detectors are approximately identical to each other and are placed adjacent to each other in the form of a matrix network to form a detection plane 44.

Furthermore, detectors 42 are located on a printed circuit board 46 and are connected to preamplifiers (not shown) on this board. Board 46 collects detection signals from the various individual detectors, shapes them and then sends them to a calculation and information processing unit 48. This unit calculates the position and energy of events. A detection head like that shown in FIG. 2 has a significantly better energy resolution than the detection head shown in FIG. 1, since the number of charges created in the semiconductor is 10 times greater than the number of light photons created in the scintillator crystal.

A gamma camera on which a detection head conform with FIG. 2 is fitted, may also be fitted with a collimator to select radiation approximately perpendicular to the detection head.

FIG. 3 shows a partial top view of a gamma camera with solid detectors on which a conventional collimator is fitted.

This figure shows the individual detectors 42 placed adjacent to each other to form the detection plane 44. Elementary individual detectors have a central part 50 sensitive to gamma radiation, and a peripheral edge (as small as possible) 52 not sensitive to gamma radiation.

A collimator 20, similar to that in FIG. 1, is located above the detection plane 44. It comprises several ducts 21 with hexagonal cross-sections, placed adjacent to each other and with a main axis approximately perpendicular to the detection plane 44. Each duct is delimited by a lead sheet folded into a hexagonal shape. The lead sheets in this shape are placed adjacent to each other and fixed together to form the collimator 20. This type of "honeycomb" structure is particularly easy to make and is well known for the manufacture of collimators like those used on "Anger" type cameras. The collimator can also be cast in a mold containing pins with a hexagonal cross-section.

Although operation of a detection head conform with FIG. 3 is generally satisfactory, the inventors have observed that its sensitivity is not uniform, and have found that this non-uniformity is due to an unequal coverage of elementary detectors by collimator ducts.

This problem is demonstrated and illustrated in FIGS. 4A, 4B, 4C and 4D.

FIGS. 4A to 4D show a top view of different relative positions of an individual detector 42 on the detection head in FIG. 3, with respect to the ducts 21 in collimator 20. For simplification reasons, a single individual detector and only part of the collimator are shown. Furthermore, the scale in FIGS. 4A to 4D is slightly greater than the scale in FIG. 3.

Calculations of the area facing the sensitive part of the detector with collimator ducts have been carried out using detectors for which the shape of the sensitive part is square with a 4 mm long side l, and for hexagonal ducts with the distance d between flats equal to 1.5 mm.

These calculations show that the facing area is 12.6 mm$^2$, 12.2 mm$^2$, 11.8 mm$^2$ and 12.6 mm$^2$, for the configurations in FIGS. 4A to 4D respectively.

To avoid non-uniformity problems in the response of the detection head, the dimensions of the hexagonal ducts can be adapted so that they cover the same active surface area of each individual detector. This requires the manufacture of a collimator using ducts with an irregular hexagonal shape. However, the manufacture of this type of collimator is difficult and expensive.

SUMMARY OF THE INVENTION

Thus, one purpose of this invention is to propose a detection head without the limitations and the disadvantages mentioned above.

Another purpose of the invention is to propose a detection head with individual detectors with semi-conductors and a uniformly-shaped collimator with uniform sensitivity.

Another purpose is to propose a collimator for a detection head with adjacent individual detectors enabling uniform detection.

In order to achieve these purposes, the purpose of the invention is more precisely a gamma camera detection head comprising:

several elementary detectors with semiconductors, approximately identical and placed adjacent to each other to form a detection plane, and, a collimator placed in front of the detection plane and consisting of a number of ducts for carrying gamma radiation, approximately identical to each other and laid out in a repetition pattern;

and in which the shape of the elementary detectors and the repetition pattern are rectangular in the detection plane, the length and width of the repetition pattern being submultiples of the length and width of the elementary detectors.

For the purposes of this invention, the length and width of the duct repetition pattern means the length and width of the ducts, including the thickness of the material walls that delimit the ducts. In the same way, the length and width of the elementary detectors means the length and width of their sensitive parts including the thickness of any insensitive "dead" areas surrounding the sensitive parts.

If insert walls are placed between the elementary detectors, the length and width of the elementary detectors are assumed to include the thickness of these walls.

Finally, note that the term rectangle is understood to be the shape of a quadrilateral in which the four corners are right angles. Thus, the shape referred to as "rectangular" also includes a square shape which is only a special case of a rectangular shape.

According to the characteristics of the invention, it is found that the sensitive area of the detector facing the collimator ducts is approximately identical for each elementary detector.

This can give excellent uniformity in the response of the detection head with this equipment.

According to particular embodiments of the detection head, the shape of the elementary detectors and/or the shape of the repetition pattern is square.

The invention also relates to a collimator for a gamma camera. The collimator according to the invention contains several ducts for carrying gamma radiation, approximately identical and parallel to each other, the ducts having a square transverse cross-section.

Finally, the invention relates to a gamma camera comprising a collimator or a detection head like those described above.

Other characteristics and advantages of the invention will become clearer from the following description with reference to the figures in the attached drawings, given for illustrative purposes and in no way restrictive.

DETAILED DESCRIPTION OF THE PREFERRED EMBODIMENTS

In the following description, parts that are identical to or similar to parts in the figures described above will have the same references plus 100.

Figure 1:
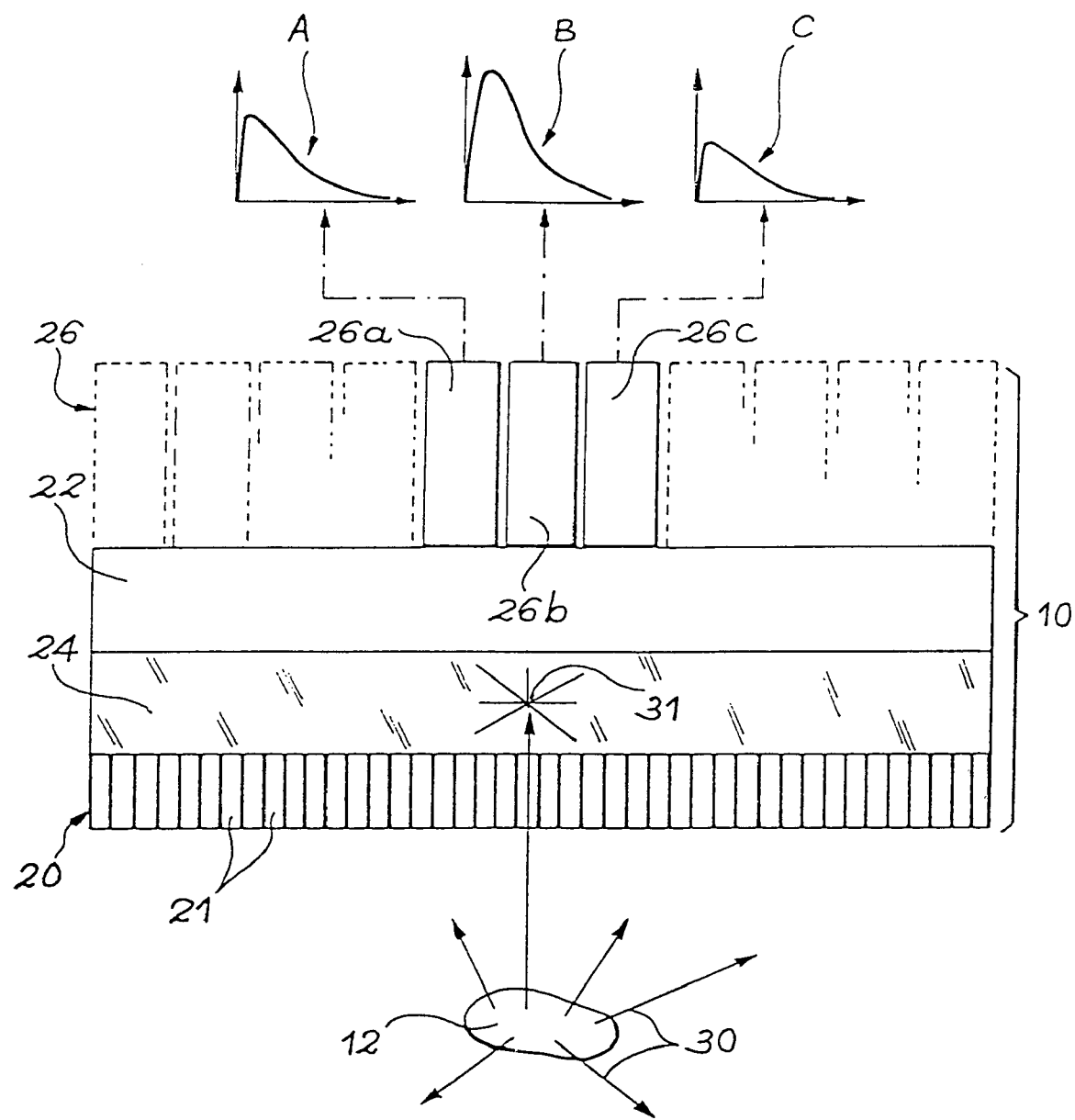
FIG. 1, described above, is a simplified diagram showing the operation of an Anger type camera equipped with a collimator.
Figure 2:
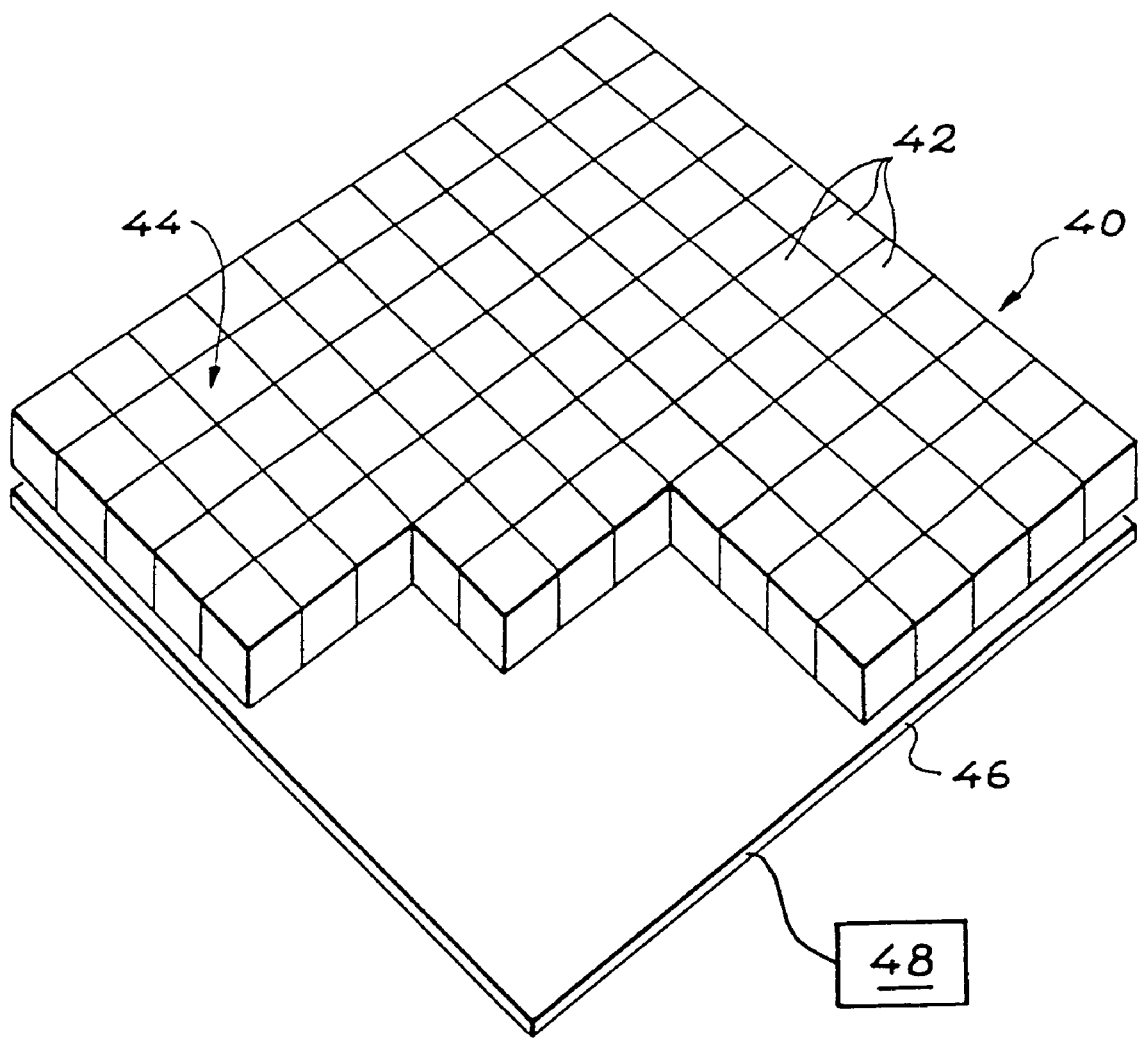
FIG. 2 diagrammatically shows a detection head with semi-conductors for gamma camera, with several individual detectors.
Figure 3:
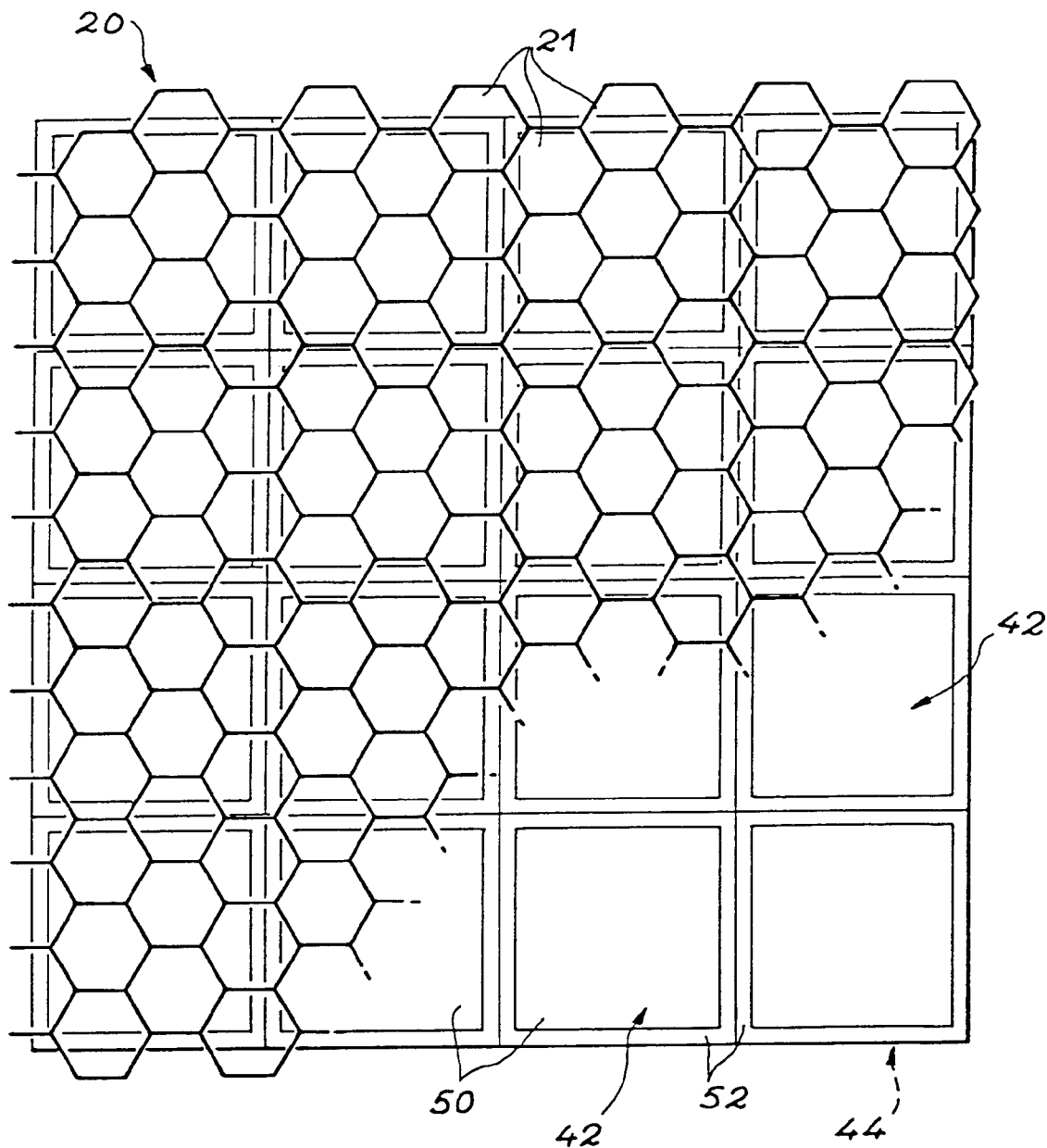
FIG. 3 is a partial top view of a detector conform with FIG. 2 equipped with a collimator with ducts with a hexagonal cross-section.
Figure 4A:
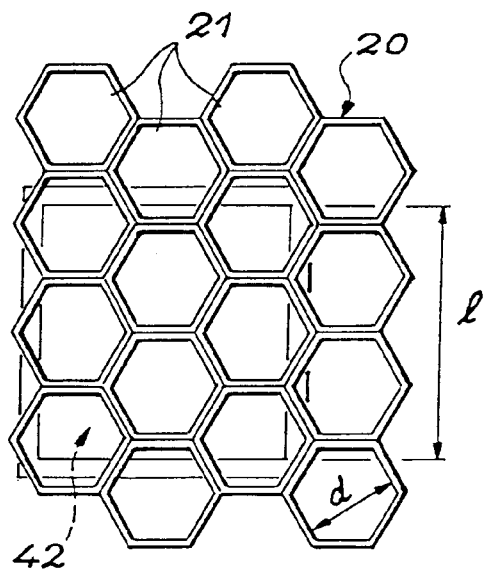
FIGS. 4A to 4D show details of different types of possible coverages between individual detectors in the detection head and collimator ducts.
Figure 4B:
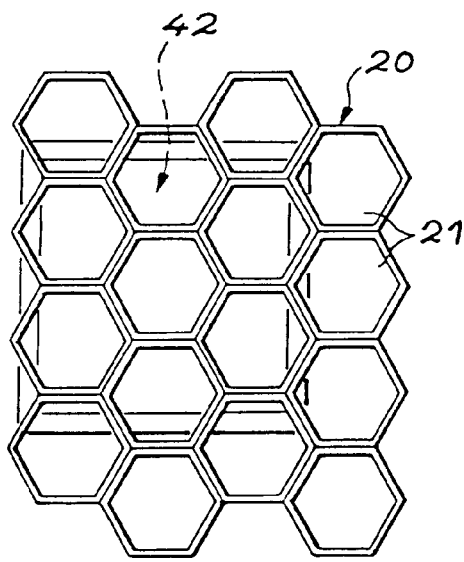
Figure 4C:
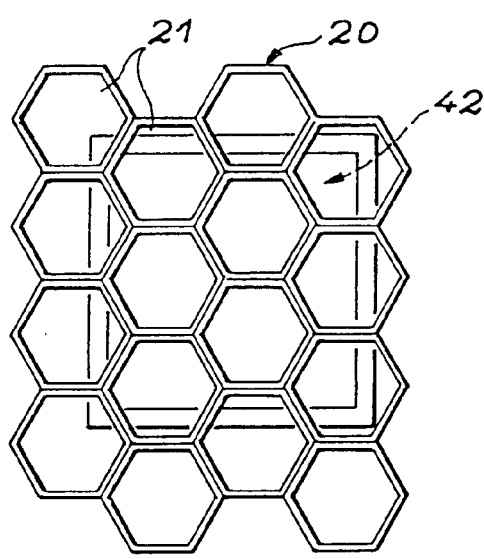
Figure 4D:
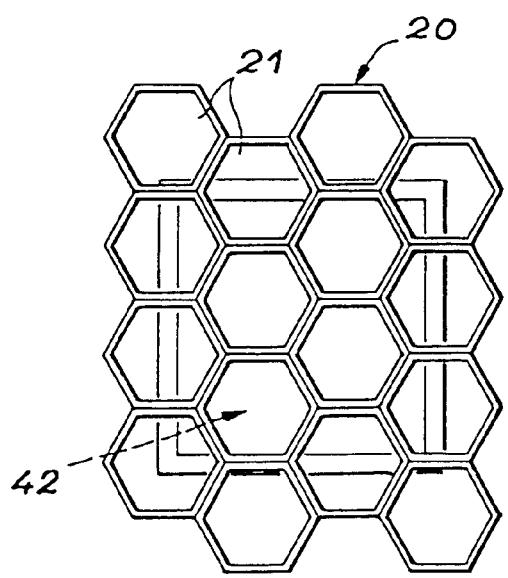
Figure 5:
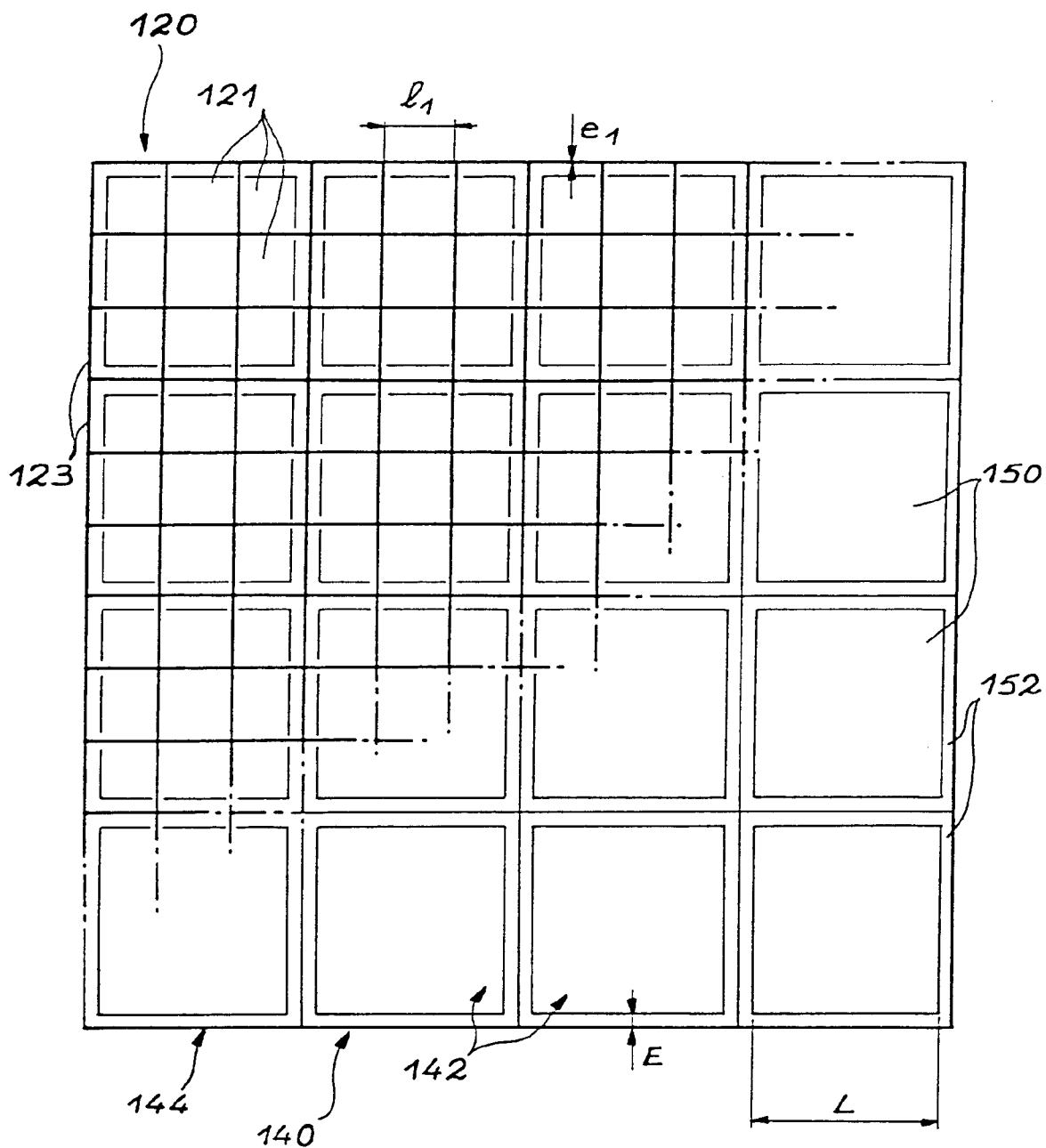
FIG. 5 is a partial diagrammatic top view of a detection head according to the invention.

As stated above, FIG. 5 is a partial top view of a detection head 140 according to the invention.

The detection head comprises a number of elementary detectors 142 placed adjacent to each other in the form of a matrix network to form a detection plane 144.

The elementary detectors 142 are CdTe or CdZnTe type detectors with semi-conductors and have a square area in the detection plane 144 with a side dimension of 3 to 5 mm.

In the example described, the surface of each detector in the detection plane 144 has a central part 150 that is sensitive to gamma radiation and an insensitive peripheral edge 152. The sensitive central part also has a square surface with a side dimension of 3 to 5 mm. This dimension is shown in the figure with reference L. The thickness E of the peripheral edge 152 is of the order of 3 mm.

The detection head also comprises preamplifier circuits to collect signals output from detectors 142 and to send them to a processing unit.

These elements are not shown in FIG. 5 for reasons of clarity.

The detection head 140 also comprises a collimator 120 placed in front of the detection plane 144. The collimator 120 may be placed directly in contact with the detection plane 144.

The collimator has a number of ducts 121 laid out perpendicular to the detection plane, in order to carry gamma radiation. Note that the ducts are not necessarily perpendicular to the detection plane, but may form a divergent or convergent bundle for a particular application.

Ducts 121 are placed adjacent to each other and are laid out according to a repetition pattern of the individual ducts, each of which has a square cross-section in the detection plane.

The side of each square cross-section is a sub-multiple of the side of the square area of the individual detectors.

In the case shown in FIG. 5, the length and width of the repetition pattern are equal to one third of the length and width of the elementary detectors in the detection plane. Thus, 9 ducts including their walls, fit into the area of each detector.

In the particular example given, each square duct 121 has an opening with a side $e_1$ of the order of 1.33 mm, and is delimited by a wall 123 with a thickness $e_1$ of the order of 0.1 mm.

It can be checked that the proportion of the area of the sensitive central part 150 intercepted by the ducts is the same for each elementary detector 142. Thus good detection uniformity is achieved.

Figure 6:
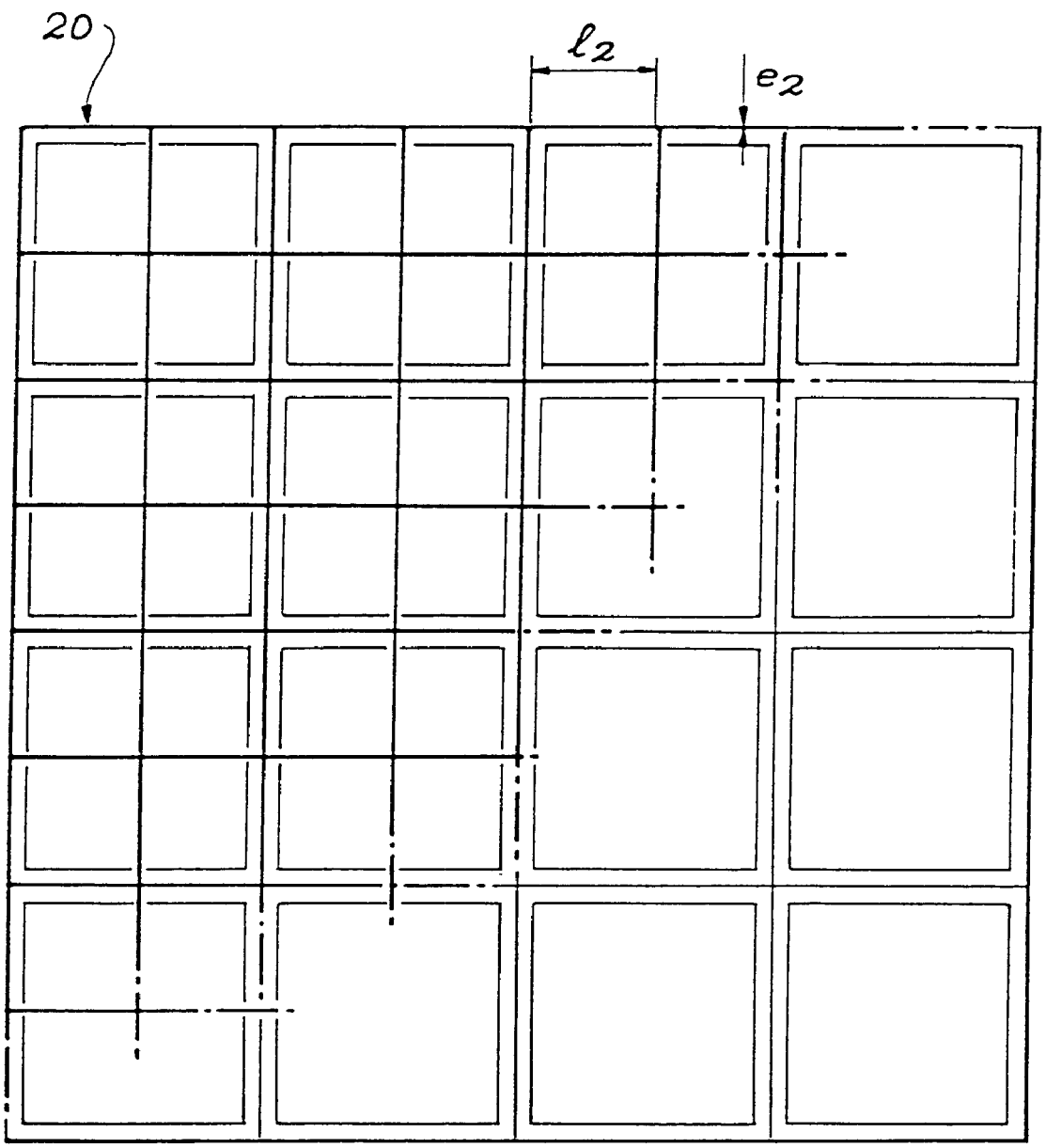
FIG. 6 is a partial diagrammatic top view of a variant embodiment of a detection head according to the invention.

FIG. 6 shows a variant embodiment of the detector according to the invention.

In the case in FIG. 6, the side (i.e., the width and length of the repetition pattern) is equal to half the side of each elementary detector in the detection plane.

The elements shown in FIG. 6, except for their dimensions, are similar to those in FIG. 5. They are denoted by the same references, and the above description contains information about them.

In the example in FIG. 6, each duct has an opening with a side $l_2$ equal to 1.7 mm and is surrounded by a wall 123 with a thickness $e_2$ of 0.3 mm.

Advantageously, collimators 120 like those shown in FIGS. 5 and 6 may be made by electro-erosion from a solid block of absorbing materials such as a solid block of lead. Electro-erosion pins with a shape corresponding to the shape of the ducts are pushed forwards into the block to form the ducts. This method facilitates manufacture of ducts with a square cross-section, and can produce sharp angles.

According to a variant, collimators conform with the invention can also be made by molding. In this case, the ducts are defined by pins with a square cross-section. These pins are preferably slightly pyramid-shaped to facilitate removing collimators from the mold.

What is claimed is:

1. Gamma camera detection head comprising:

elementary semiconductor detectors, approximately identical and placed adjacent to each other to form a detection plane; and a collimator placed in front of the detection plane, including a number of ducts configured to carry gamma radiation, each duct approximately identical to each other and laid out in a repetition pattern, wherein a shape of the elementary detectors and the repetition pattern are rectangular in the detection plane and a length and a width of the repetition pattern are sub-multiples of a length and a width of the elementary detectors.

2. Detection head according to claim 1, wherein at least one of the shape of the elementary detectors and the shape of the repetition pattern is square in the detection plane.

3. Detection head according to claim 2, wherein the width and length of the repetition pattern is equal to one third of the width and length of the individual detectors.

4. Detection head according to claim 2, wherein the width and length of the repetition pattern is equal to half the width and length of the individual detectors.

5. Gamma camera collimator comprising:
a number of ducts configured to carry gamma radiation to elementary detectors, said ducts approximately identical with and parallel to each other and laid out in a repetition pattern, the ducts having a square transverse cross-section and having a length and a width of the repetition pattern which are sub-multiples of a length and a width of the elementary detectors.

6. Gamma camera comprising a collimator according to claim 5.

7. Gamma camera comprising a detection head according to one of claims 1 to 4.

* * * * *